US010426882B2

United States Patent
Kelly et al.

(10) Patent No.: US 10,426,882 B2
(45) Date of Patent: Oct. 1, 2019

(54) BLOOD RINSEBACK SYSTEM AND METHOD

(71) Applicants: Baxter International Inc., Deerfield, IL (US); Baxter Healthcare S.A., Glattpark (Opfikon) (CH)

(72) Inventors: Thomas D. Kelly, Tampa, FL (US); Waleed M. El Sayyid, Odessa, FL (US)

(73) Assignees: Baxter International Inc., Deerfield, IL (US); Baxter Healthcare SA, Glattpark (Opfikon) (CH)

( * ) Notice: Subject to any disclaimer, the term of this patent is extended or adjusted under 35 U.S.C. 154(b) by 0 days.

(21) Appl. No.: 16/266,924

(22) Filed: Feb. 4, 2019

(65) Prior Publication Data

US 2019/0167884 A1    Jun. 6, 2019

Related U.S. Application Data (60) Continuation of application No. 14/967,646, filed on Dec. 14, 2015, now Pat. No. 10,195,332, which is a
(Continued)

(51) Int. Cl.
*A61M 1/34* (2006.01)
*A61M 1/16* (2006.01)
(Continued)

(52) U.S. Cl.
CPC ........ *A61M 1/3462* (2013.01); *A61M 1/1601* (2014.02); *A61M 1/1635* (2014.02);
(Continued)

(58) Field of Classification Search
CPC ........ A61M 1/1635; A61M 1/30; A61M 1/34; A61M 1/3403; A61M 1/341;
(Continued)

(56) References Cited

U.S. PATENT DOCUMENTS 2,442,938 A    9/1945    Ruge
3,292,077 A    12/1966   Sloughter
(Continued)

FOREIGN PATENT DOCUMENTS

DE    2019147    10/1970
DE    2703188    8/1978
(Continued)

OTHER PUBLICATIONS

Brochure titled, "Blood Lines, CAVH/D Systems and Accessories," from the company Fresenius Medical Care Mar. 2001 (4 pages).
(Continued)

*Primary Examiner* — Leslie R Deak
(74) *Attorney, Agent, or Firm* — K&L Gates LLP (57) ABSTRACT

A hemodialysis system is provided and includes a dialyzer, a dialysis fluid circuit in fluid communication with the dialyzer, a blood circuit, a blood detector and a blood rinseback scheme, wherein the blood rinseback scheme includes transferring blood to the patient using a physiologically acceptable fluid, wherein the physiologically acceptable fluid is introduced from its source into an arterial line between an arterial line patient end and a blood pump of the blood circuit, and flowed through the dialyzer, through a venous drip chamber and to the blood detector along a venous line of the blood circuit, where the physiologically acceptable fluid is sensed by the blood detector to indicate an end of the blood rinseback.

21 Claims, 5 Drawing Sheets

Related U.S. Application Data continuation of application No. 13/833,903, filed on Mar. 15, 2013, now Pat. No. 9,211,370, which is a continuation of application No. 12/793,906, filed on Jun. 4, 2010, now Pat. No. 8,430,835, which is a division of application No. 10/738,446, filed on Dec. 16, 2003, now Pat. No. 7,744,553.

(51) Int. Cl.
*A61M 1/36* (2006.01)
*A61M 1/30* (2006.01)

(52) U.S. Cl.
CPC ............ *A61M 1/1672* (2014.02); *A61M 1/34* (2013.01); *A61M 1/341* (2014.02); *A61M 1/3403* (2014.02); *A61M 1/3413* (2013.01); *A61M 1/3434* (2014.02); *A61M 1/3643* (2013.01); *A61M 1/3644* (2014.02); *A61M 1/3647* (2014.02); *A61M 1/3649* (2014.02); *A61M 1/30* (2013.01); *A61M 2205/3303* (2013.01); *A61M 2205/3306* (2013.01); *A61M 2205/50* (2013.01); *A61M 2205/7518* (2013.01)

(58) Field of Classification Search
CPC ............... A61M 1/3434; A61M 1/3462; A61M 1/3643; A61M 1/3644; A61M 1/3649; A61M 2205/3306; A61M 2205/50
See application file for complete search history.

(56) References Cited

U.S. PATENT DOCUMENTS

| | | |
|---|---|---|
| 3,387,209 A | 6/1968 | Eames et al. |
| 3,396,331 A | 8/1968 | Sperry, III |
| 3,404,336 A | 10/1968 | Rosenthal |
| 3,441,136 A | 4/1969 | Serfass et al. |
| 3,461,416 A | 8/1969 | Kaufman |
| 3,601,255 A | 8/1971 | Pecker et al. |
| 3,669,880 A | 6/1972 | Marantz et al. |
| 3,726,793 A | 4/1973 | Bray |
| 3,738,356 A | 6/1973 | Workman |
| 3,753,493 A | 8/1973 | Mellor |
| 3,818,765 A | 6/1974 | Eriksen |
| 3,831,588 A | 8/1974 | Rinder |
| 3,871,913 A | 3/1975 | Shaldon |
| 3,898,017 A | 8/1975 | Mandroian |
| 3,920,030 A | 11/1975 | Mason |
| 3,939,069 A | 2/1976 | Granger et al. |
| 3,979,284 A | 9/1976 | Granger et al. |
| 3,980,946 A | 9/1976 | Fleury |
| 4,017,190 A | 4/1977 | Fischel |
| 4,024,059 A | 5/1977 | Sausse |
| 4,077,882 A | 3/1978 | Gangemi |
| 4,085,047 A | 4/1978 | Thompson |
| 4,087,185 A | 5/1978 | Lamadrid |
| 4,132,644 A | 1/1979 | Kolberg |
| 4,138,639 A | 2/1979 | Hutchins |
| 4,166,961 A | 9/1979 | Dam et al. |
| 4,178,240 A | 12/1979 | Pinkerton |
| 4,204,957 A | 5/1980 | Weickhardt |
| 4,220,920 A | 9/1980 | Gross |
| 4,227,420 A | 10/1980 | Lamadrid |
| 4,298,938 A | 11/1981 | Wang et al. |
| 4,314,480 A | 2/1982 | Becker |
| 4,324,663 A | 4/1982 | Hirel et al. |
| 4,371,385 A | 2/1983 | Johnson |
| 4,372,846 A | 2/1983 | Yamagami et al. |
| 4,379,452 A | 4/1983 | De Vries |
| 4,398,542 A | 8/1983 | Cunningham et al. |
| 4,399,030 A | 8/1983 | Hlavinka et al. |
| 4,411,783 A | 10/1983 | Dickens et al. |
| 4,412,916 A | 11/1983 | Kell |
| 4,444,597 A | 4/1984 | Gortz et al. |
| 4,460,355 A | 7/1984 | Layman |
| 4,468,329 A | 8/1984 | Shaldon et al. |
| 4,469,593 A | 9/1984 | Ishihara et al. |
| 4,477,342 A | 10/1984 | Allan et al. |
| 4,515,606 A | 5/1985 | De Winter |
| 4,517,081 A | 5/1985 | Amiot et al. |
| 4,526,515 A | 7/1985 | De Vries |
| 4,526,574 A | 7/1985 | Pekkarinen |
| 4,545,389 A | 10/1985 | Schaberg et al. |
| 4,552,721 A | 11/1985 | Fentress et al. |
| 4,572,724 A | 2/1986 | Rosenberg et al. |
| 4,582,598 A | 4/1986 | Bilstad et al. |
| 4,600,401 A | 7/1986 | Kamen |
| 4,606,826 A | 8/1986 | Sano et al. |
| 4,610,782 A | 9/1986 | Tersteegen et al. |
| 4,650,458 A | 3/1987 | Dahlberg et al. |
| 4,661,246 A | 4/1987 | Ash |
| 4,670,152 A | 6/1987 | Leonard |
| 4,676,467 A | 6/1987 | Palsulich |
| 4,676,771 A | 6/1987 | Henke |
| 4,676,905 A | 6/1987 | Nagao et al. |
| 4,681,606 A | 7/1987 | Swan, Jr. et al. |
| 4,684,460 A | 8/1987 | Issautier |
| 4,680,762 A | 9/1987 | Katsura |
| 4,695,385 A | 9/1987 | Boag |
| 4,702,829 A | 10/1987 | Polaschegg et al. |
| 4,708,802 A | 11/1987 | Rath et al. |
| 4,711,715 A | 12/1987 | Polaschegg |
| 4,728,433 A | 3/1988 | Buck et al. |
| 4,734,269 A | 3/1988 | Clarke et al. |
| 4,740,755 A | 4/1988 | Ogawa |
| 4,758,337 A | 7/1988 | Kohn et al. |
| 4,767,399 A | 8/1988 | Bollish |
| 4,769,132 A | 9/1988 | Patono |
| 4,770,769 A | 9/1988 | Schael |
| 4,770,787 A | 9/1988 | Heath et al. |
| 4,784,495 A | 11/1988 | Jonsson et al. |
| 4,784,576 A | 11/1988 | Bloom et al. |
| 4,798,090 A | 1/1989 | Heath et al. |
| 4,825,168 A | 4/1989 | Ogawa et al. |
| 4,834,888 A | 5/1989 | Polaschegg |
| 4,838,865 A | 6/1989 | Flank et al. |
| 4,844,810 A | 7/1989 | Richalley et al. |
| 4,850,998 A | 7/1989 | Schoendorfer |
| 4,889,635 A | 12/1989 | Chevallet |
| 4,919,802 A | 4/1990 | Katsura |
| 4,923,598 A | 5/1990 | Schal |
| 4,925,299 A | 5/1990 | Meisberger et al. |
| 4,932,987 A | 6/1990 | Molina |
| 4,964,984 A | 10/1990 | Reeder et al. |
| 4,980,054 A | 12/1990 | Lavender |
| 4,995,268 A | 2/1991 | Ash et al. |
| 4,997,570 A | 3/1991 | Polescegg |
| 5,001,548 A | 4/1991 | Richalley et al. |
| 5,015,226 A | 5/1991 | Polaschegg |
| 5,032,265 A | 7/1991 | Jha et al. |
| 5,041,215 A | 8/1991 | Chamberlain, Jr. et al. |
| 5,045,096 A | 9/1991 | Quang et al. |
| 5,061,236 A | 10/1991 | Sutherland et al. |
| 5,092,836 A | 3/1992 | Polaschegg |
| 5,110,477 A | 5/1992 | Howard et al. |
| 5,114,580 A | 5/1992 | Ahmad et al. |
| 5,173,125 A | 12/1992 | Felding |
| 5,178,763 A | 1/1993 | Delaunay |
| 5,186,431 A | 2/1993 | Tamari |
| 5,203,368 A | 4/1993 | Barstow et al. |
| 5,211,849 A | 5/1993 | Kitavich et al. |
| 5,252,213 A | 10/1993 | Ahmad et al. |
| 5,259,961 A | 11/1993 | Eigendorf |
| 5,331,958 A | 7/1994 | Oppenheimer |
| 5,336,165 A | 9/1994 | Twardowski |
| 5,344,568 A | 9/1994 | Kitavich et al. |
| 5,366,630 A | 11/1994 | Chevallet |
| 5,383,249 A | 1/1995 | Yang |
| 5,392,653 A | 2/1995 | Zanger et al. |
| 5,431,626 A | 7/1995 | Bryant et al. |
| 5,470,483 A | 11/1995 | Bene et al. |
| 5,520,640 A | 5/1996 | Utterberg |

(56) References Cited

U.S. PATENT DOCUMENTS

| | | | |
|---|---|---|---|
| 5,522,998 | A | 6/1996 | Polaschegg |
| 5,529,685 | A | 6/1996 | Irie et al. |
| 5,591,344 | A | 1/1997 | Kenley et al. |
| 5,614,677 | A | 3/1997 | Wamsiedler et al. |
| 5,630,946 | A | 5/1997 | Hart et al. |
| 5,650,071 | A | 7/1997 | Brugger et al. |
| 5,660,722 | A | 8/1997 | Nederlof |
| 5,690,831 | A | 11/1997 | Kenley et al. |
| 5,702,597 | A | 12/1997 | Chevallet et al. |
| 5,733,257 | A | 3/1998 | Sternby |
| 5,776,345 | A | 7/1998 | Trutt et al. |
| 5,783,072 | A | 7/1998 | Kenley et al. |
| 5,824,213 | A | 10/1998 | Utterberg |
| 5,836,908 | A | 11/1998 | Beden et al. |
| 5,846,419 | A | 12/1998 | Nederlof |
| 5,895,368 | A | 4/1999 | Utterberg |
| 5,919,369 | A | 7/1999 | Ash |
| 5,932,103 | A | 8/1999 | Kenley et al. |
| 6,042,784 | A | 3/2000 | Wamsiedler et al. |
| 6,077,443 | A | 6/2000 | Goldau |
| 6,132,616 | A | 10/2000 | Twardowski et al. |
| 6,139,748 | A | 10/2000 | Ericson et al. |
| 6,254,567 | B1 | 7/2001 | Treu et al. |
| 6,280,632 | B1 | 8/2001 | Polaschegg |
| 6,287,516 | B1 | 9/2001 | Matson et al. |
| 6,387,069 | B1 | 5/2002 | Utterberg |
| 6,495,366 | B1 | 12/2002 | Briggs |
| 6,591,997 | B2 | 5/2003 | Weitzel et al. |
| 6,572,576 | B2 | 6/2003 | Brugger et al. |
| 6,582,385 | B2 | 6/2003 | Burbank et al. |
| 6,595,943 | B1 | 7/2003 | Burbank |
| 6,620,120 | B2 | 9/2003 | Laundry et al. |
| 6,638,477 | B1 | 10/2003 | Treu et al. |
| 6,649,063 | B2 | 11/2003 | Brugger et al. |
| 6,821,441 | B2 | 11/2004 | Pedrini et al. |
| 6,824,524 | B1 | 11/2004 | Favre |
| 6,830,553 | B1 | 12/2004 | Burbank et al. |
| 6,843,779 | B1 | 1/2005 | Andrysiak et al. |
| 6,852,090 | B2 | 2/2005 | Burbank et al. |
| 6,916,424 | B2 | 7/2005 | Collins et al. |
| 7,214,312 | B2 | 5/2007 | Brugger et al. |
| 7,494,590 | B2 | 2/2009 | Felding et al. |
| 7,727,176 | B2 | 6/2010 | Tonelli et al. |
| 7,744,553 | B2 | 6/2010 | Kelly et al. |
| 7,850,856 | B2 | 12/2010 | Zhang et al. |
| 7,935,074 | B2 | 5/2011 | Plahey et al. |
| 7,981,280 | B2 | 7/2011 | Carr et al. |
| 8,029,454 | B2 | 10/2011 | Kelly et al. |
| 8,192,401 | B2 | 6/2012 | Morris et al. |
| 8,197,231 | B2 | 6/2012 | Orr |
| 8,720,913 | B2 | 5/2014 | Fallon et al. |
| 9,186,449 | B2 | 11/2015 | Singh et al. |
| 9,328,969 | B2 | 5/2016 | Wraxel et al. |
| 9,402,945 | B2 | 8/2016 | Hogard et al. |
| 9,500,188 | B2 | 11/2016 | Ly et al. |
| 9,545,469 | B2 | 1/2017 | Curtis et al. |
| 9,561,323 | B2 | 2/2017 | Plahey et al. |
| 9,610,392 | B2 | 4/2017 | Farrell et al. |
| 9,624,915 | B2 | 4/2017 | Medina |
| 9,694,125 | B2 | 7/2017 | Plahey et al. |
| 10,117,985 | B2 | 11/2018 | Ly et al. |
| 2001/0021817 | A1 | 9/2001 | Brugger et al. |
| 2001/0037079 | A1 | 11/2001 | Burbank et al. |
| 2002/0104800 | A1 | 8/2002 | Collins et al. |
| 2002/0121471 | A1 | 9/2002 | Pedrazzi |
| 2002/0151834 | A1 | 10/2002 | Utterberg |
| 2003/0018290 | A1 | 1/2003 | Brugger et al. |
| 2004/0025597 | A1 | 2/2004 | Ericson et al. |
| 2004/0158189 | A1 | 8/2004 | Tonelli et al. |
| 2004/0233049 | A1 | 11/2004 | Harada et al. |
| 2004/0243046 | A1 | 12/2004 | Brugger et al. |
| 2004/0243050 | A1 | 12/2004 | Treu et al. |
| 2004/0245161 | A1 | 12/2004 | Treu et al. |
| 2004/0267184 | A1 | 12/2004 | Burbank et al. |
| 2004/0267185 | A1 | 12/2004 | Weaver et al. |
| 2005/0000868 | A1 | 1/2005 | Weigel et al. |
| 2005/0004502 | A1 | 1/2005 | O'Mahoney et al. |
| 2005/0011823 | A1 | 1/2005 | Delveno et al. |
| 2006/0237351 | A1 | 10/2006 | Felding |
| 2006/0254982 | A1 | 11/2006 | Kopperschmidt |
| 2009/0088675 | A1 | 4/2009 | Kelly et al. |
| 2009/0124963 | A1 | 5/2009 | Hogard et al. |
| 2009/0294359 | A1 | 12/2009 | Hopping et al. |
| 2010/0274168 | A1 | 10/2010 | Gronau et al. |
| 2016/0263306 | A1 | 9/2016 | Kelly et al. |
| 2018/0036472 | A1 | 2/2018 | Kelly et al. |

FOREIGN PATENT DOCUMENTS

| | | |
|---|---|---|
| DE | 3442744 | 6/1986 |
| DE | 4240681 | 6/1994 |
| DE | 19704564 | 8/1998 |
| DE | 10011208 | 9/2001 |
| DE | 10213179 | 8/2003 |
| DE | 10224750 | 12/2003 |
| DE | 102005058012 | 6/2007 |
| DE | 102006022122 | 11/2007 |
| DE | 102006042120 | 4/2008 |
| DE | 102009012633 | 9/2010 |
| DE | 102010053973 | 6/2012 |
| DE | 102014109136 | 12/2015 |
| EP | 0189561 | 8/1986 |
| EP | 0192588 | 8/1986 |
| EP | 0228160 | 7/1987 |
| EP | 0321754 | 6/1989 |
| EP | 0373455 | 6/1990 |
| EP | 0560368 | 9/1993 |
| EP | 0578175 | 1/1994 |
| EP | 0597817 | 5/1994 |
| EP | 1110564 | 6/2001 |
| EP | 1175917 | 1/2002 |
| EP | 1344542 | 3/2003 |
| EP | 1433490 | 12/2003 |
| EP | 1699505 | 9/2006 |
| EP | 2745864 | 6/2014 |
| FR | 2390173 | 12/1978 |
| FR | 2397197 | 2/1979 |
| GB | 831692 | 3/1960 |
| JP | H07100199 | 4/1995 |
| JP | 2002045420 | 2/2002 |
| JP | 5247864 | 7/2013 |
| JP | 5519427 | 6/2014 |
| JP | 5914106 | 5/2016 |
| JP | 6017713 | 10/2016 |
| JP | 6017711 | 11/2016 |
| JP | 6017712 | 11/2016 |
| JP | 6062580 | 1/2017 |
| WO | 85038979 | 9/1985 |
| WO | 9115253 | 10/1991 |
| WO | 9709074 | 3/1997 |
| WO | 9929355 | 6/1999 |
| WO | 0051664 | 9/2000 |
| WO | 2001032238 | 5/2001 |
| WO | 2001051106 | 7/2001 |
| WO | 03047656 | 6/2003 |
| WO | 2004069311 | 8/2004 |
| WO | 2011008858 | 1/2011 |
| WO | 2012154352 | 11/2012 |
| WO | 2013092011 | 6/2013 |

OTHER PUBLICATIONS

English translation of Fresenius Medical Care AG & Co. KGaA's Opposition against EP1699505B1 dated Nov. 26, 2014 (26 pages).
Manns et al., "The acu-menTM: A new device for continuous renal replacement therapy in acute renal failure," Kidney International, 1998, pp. 268-274, vol. 54.

FLUID IN  DWELL  FLUID OUT

BLOOD RINSEBACK SYSTEM AND METHOD

PRIORITY

This application claims priority to and the benefit as a continuation application of U.S. patent application Ser. No. 14/967,646, entitled "Renal Therapy Blood Cleansing System With Selective Valve Feature", filed Dec. 14, 2015, which is a continuation of U.S. patent application Ser. No. 13/833,903, entitled, "Renal Therapy Blood Cleansing System with Isolation Feature", filed Mar. 15, 2013, now U.S. Pat. No. 9,211,370, issued Dec. 15, 2015, which is a continuation application of U.S. patent application Ser. No. 12/793,906, entitled, "Renal Therapy Blood Cleansing System with Balance Chamber and Bolus, Rinseback or Prime Volume Feature", filed Jun. 4, 2010, now U.S. Pat. No. 8,430,835, issued Apr. 30, 2013, which is a divisional application of U.S. patent application Ser. No. 10/738,446, entitled, "Medical Fluid Therapy Fluid Therapy Flow Control Systems and Methods", filed Dec. 16, 2003, now U.S. Pat. No. 7,744,553, issued Jun. 29, 2010, the entire contents of each of which are incorporated herein by reference and relied upon.

BACKGROUND OF THE INVENTION

The present invention relates to medical systems and more particularly to medical fluid treatment therapies.

Due to disease, injury or other causes, a person's renal system can fail. In renal failure of any cause, there are several physiological derangements. The balance of water, minerals and the excretion of daily metabolic load are reduced or no longer possible in renal failure. During renal failure, toxic end products of nitrogen metabolism (e.g., urea, creatinine, uric acid, and others) can accumulate in blood and tissues.

Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life sustaining. One who has failed kidneys could not continue to live without replacing at least the filtration functions of the kidneys.

Hemodialysis ("HD"), hemofiltration ("HF"), hemodiafiltration ("HDF") and peritoneal dialysis ("PD") are types of dialysis therapies generally used to treat loss of kidney function. Peritoneal dialysis utilizes a sterile dialysis solution, or "dialysate", which is infused into a patient's peritoneal cavity and into contact with the patient's peritoneal membrane. Waste, toxins and excess water pass from the patient's bloodstream through the peritoneal membrane and into the dialysate. The transfer of waste, toxins, and excess water from the bloodstream into the dialysate occurs due to diffusion and osmosis during a dwell period as an osmotic agent in the dialysate creates an osmotic gradient across the membrane. The spent dialysate is later drained from the patient's peritoneal cavity to remove the waste, toxins and excess water from the patient.

Hemodialysis treatment removes waste, toxins and excess water directly from the patient's blood. The patient is connected to a hemodialysis machine and the patient's blood is pumped through the machine. Needles or catheters are inserted into the patient's veins and arteries to create a blood flow path to and from the hemodialysis machine. As blood passes through a dialyzer in the hemodialysis machine, the dialyzer removes the waste, toxins and excess water from the patient's blood and returns the cleansed blood back to the patient. A large amount of dialysate, for example about ninety to one hundred twenty liters, is used by most hemodialysis machines to dialyze the blood during a single hemodialysis therapy. Spent dialysate is discarded. Hemodialysis treatment lasts several hours and is generally performed in a treatment center about three times per week.

Hemofiltration is an effective convection-based blood cleansing technique. Blood access can be venovenous or arteriovenous. As blood flows through the hemofilter, a transmembrane pressure gradient between the blood compartment and the ultrafiltrate compartment causes plasma water to be filtered across the highly permeable membrane. As the water crosses the membrane, it convects small and large molecules across the membrane and thus cleanses the blood. A large amount of plasma water is eliminated by filtration. Therefore, in order to keep the body water balanced, fluid must be substituted continuously by a balanced electrolyte solution (replacement or substitution fluid) infused intravenously. This substitution fluid can be infused either into the arterial blood line leading to the hemofilter (predilution), into the venous blood line leaving the hemofilter (postdilution) or both. Another type of therapy, hemodiafiltration, combines the diffusion and convective cleansing modes of hemodialysis and hemofiltration.

A patient's hematocrit, which is the percentage of red blood cells in the blood, is about thirty-two to thirty-six percent by volume, leaving the amount of fluid in the blood to range from about sixty-four to sixty-eight percent. In a typical HDF and HF therapy, blood flow can be about 300 ml/min, wherein about 100 ml/min of the fluid is being removed through the filter, leaving a relatively smaller percentage of the blood as fluid to exit the hemofilter and to thereafter receive an amount of dialysate.

Postdilution is a more efficient blood clearance mode than predilution HF or HDF. In some instances, postdilution HF or HDF can be fifty percent more efficient than predilution HF or HDF. With postdilution clearance, however, blood exits the body and enters the filter before the extracorporeal circuit receives therapy fluid or dialysate. Because the hemodialyzer or hemofilter can remove a good portion of the liquid from the patient's blood, postdilution clearance can hemoconcentrate or clot the blood filter. Predilution clearance, on the other hand, infuses fresh therapy fluid into the extracorporeal circuit before the filter and therefore at least substantially reduces the possibility that blood will clot in the hemofilter or hemodialyzer.

With predilution HF or HDF, the dialysate is fed into the extracorporeal circuit prior to the hemofilter. Some of that fluid is then immediately removed by the filter, rendering the therapy less effective than postdilution therapy. Blood leaving the filter, however, has the same percentage liquid, e.g., sixty-four to sixty-eight percent, as the blood leaving the patient, reducing the chances of clotting or aggregating blood platelets because the blood has too high a percentage of solids.

It is therefore desirable to provide a hemofiltration and/or a hemodiafiltration system that can perform both predilution or postdilution clearance modes.

It is also desirable to provide an HF and/or an HDF system that provides a priming function, bolus infusion function and/or a blood rinseback function. System priming occurs at the beginning of therapy to remove air from the line, which would be harmful if delivered to the patient. The prime purges the air with a sterile or substantially sterile electrolyte solution.

At certain times during HF or HDF therapy it is necessary to deliver a bolus or relatively large volume of fluid to the patient. It may happen during therapy that too much blood is removed from the patient too quickly. The patient's vascular space contains only five to six liters of blood. Removing too much blood too quickly can possibly lower the pressure in the vascular space. The patient's heart rate will quicken and the vascular system will contract in an attempt to compensate for the loss in blood pressure, however, such measures may not be enough to prevent the patient from becoming hypotensive. In such a case, providing a bolus or volume of fluid to the patient is one effective procedure for increasing the blood pressure in the vascular system.

It is further desirable to have an HF or HDF system that can provide a blood rinseback at the end of therapy. At the end of therapy there is typically blood that remains in the extracorporeal circuit. It is desirable to return as much of that blood as possible to the patient. To do so, the blood therapy system needs to have the ability to pass a volume of fluid through the blood circuit sufficient to push the blood remaining therein back to the patient.

Both the bolus feature and the rinseback feature present challenges to the machine manufacturer. For instance, if the machine uses a fluid balancing system or match flow equalizer that removes an equal amount of fluid from the patient for each amount of fluid delivered to the patient, that balancing system must be accounted for to enable a positive net fluid volume to be delivered to the patient. Second, since the fluid is delivered directly to the extracorporeal circuit, the bolus or rinseback fluid needs to be sterile or of an injectable quality.

Removing ultrafiltrate ("UF") from the patient is a precise operation in which a specific amount of fluid needs to be removed from the patient over the course of therapy. The amount of fluid removed from the patient therefore needs to be carefully monitored. In that regard, problems arise if the device or devices controlling the UF rate or volume output fails, e.g., if a valve fails. In such a case, uncontrolled flow from the patient can occur causing an overfiltration of the patient. It is therefore desirable to have an ultrafiltration flow control device that fails in such a way that fluid flow is blocked and uncontrolled UF removal does not occur.

Certain HF and HDF machines generate the fluid used during therapy at the time and place that the therapy takes place. Those machines are referred to as "on-line" machines because they make and provide the solution on-line. On-line machines use micro or ultrafilters to sterilize the solution or make it of an injectable quality before the solution is delivered to the patient's extracorporeal circuit. The filters over time accumulate bacteria and endotoxin along the outer filtering surfaces of the membranes located inside the filters. It is therefore desirable to have a method and apparatus that cleans or at least reduces the amount of bacteria and endotoxin that accumulate and reside along the membranes of the filters used to create dialysate on-line.

SUMMARY OF THE INVENTION

The present invention provides systems and methods for improving medical fluid delivery systems, such as hemodialysis ("HD"), hemofiltration ("HF") and hemodiafiltration ("HDF") systems. The present invention includes a multitude of aspects relating to medical fluid flow. In one aspect, systems and methods for selectively performing pre- and postdilution HF and HDF clearance modes are provided. In another aspect, systems and methods for providing priming, bolus and rinseback fluid volumes during/after HF and HDF therapies are provided. In a further primary aspect, improved systems and methods for removing ultrafiltrate from the patient are provided. In still a further aspect, the present invention provides an improved filtration configuration and method.

In one aspect of the present invention, an HF or HDF system is provided that performs pre- and/or postdilution clearance modes, e.g., concurrently or simultaneously. The system efficiently uses flow components to perform both pre- and postdilution clearance modes. For example, the system does not require an extra pump or an additional pump segment to be located in the substitution fluid line, wherein such additional components would have to be integrated into the machine to react appropriately to alarms and operator settings, etc.

The pre/postdilution feature of the present invention instead uses a "Y" connector located at the output of the system's substitution line. A first leg of the "Y" connector extends to the postdilution drip chamber. A first check valve is placed on the first leg to prevent blood from backing into the first leg or substitution fluid infusion line. The second leg of the "Y" can be used for multiple purposes, such as for a connection to the predilution drip chamber or the arterial line to prime the extracorporeal circuit. In the present invention, the second leg is used to deliver dialysate, prefilter, to the blood line. A second check valve is accordingly placed on the second leg to prevent blood from backing into the substitution line.

Two substitution line pinch clamps are provided, one for each leg output of the "Y" connector. In one embodiment, when pre- and postdilution are desired during the same therapy, the arterial line is primed. When the patient or nurse is ready to connect the dialysate lines to the dialyzer, the second leg of the "Y" connector is connected fluidly to an arterial drip chamber located upstream from the blood pump. The first leg of the "Y" connector is connected fluidly to the venous drip chamber. The electrically or pneumatically actuated substitution line pinch clamps placed on each of the first and second legs extending from the "Y" connector control the amount of substitution fluid used for predilution and postdilution infusion.

In one embodiment, the operator sets a total target substitution fluid volume that the patient is to receive. In addition, the operator inputs a percentage pre- versus postdilution setting, for example, by setting a specific predilution volume or flowrate or postdilution volume or flowrate or enters a percent predilution versus a percent postdilution. Upon starting therapy, the single substitution pump runs continuously, while the clamps alternate to achieve the desired pre- and postdilution percentage. For example, if the total substitution flowrate is 150 milliliters/minute ("ml/min") and a fifty ml/min substitution predilution flowrate is desired, the postdilution clamp could be closed while the predilution clamp is opened for, e.g., five seconds, followed by the predilution clamp being closed and the postdilution clamp being opened for ten seconds. The result is a continuously running flow of fluid into one of the arterial or venous drip chambers, for example, to perform postdilution therapy a majority of the time for its improved clearance ability, while performing predilution therapy enough of the time to prevent blood clotting and hypotension.

The system is provided with suitable alarms and assurances, such as a sensor that senses if one or both the clamps is in the wrong position, e.g., both clamps being closed at the same time. In such a case, the machine sends an appropriate alarm and takes an appropriate evasive action. There are many alternative technologies to sense clamp position, such as via a microswitch, Reed switch, Hall effect switch, optical sensing, ultrasonic sensing, pressure transducer and the like.

In another aspect of the present invention, an HF/HDF system is provided that performs special fluid delivery functions, such as a prime, a bolus function and a blood rinseback using fluid components in an efficient arrangement. Those function can be commenced manually or automatically, e.g., upon receipt of a signal from a suitable biosensor. In one embodiment, a two-way isolate valve is placed in the post dialyzer therapy fluid or dialysate circuit. The isolate valve is electrically or pneumatically controlled by the machine controller to perform one of a plurality of functions at a desired time in therapy.

In one implementation, the isolate valve is used to perform a bolus infusion, e.g., to stabilize the patient who has low blood pressure or is hypotensive. The bolus amount can be predetermined or entered at the time it is needed. Upon an operator input or suitable signal from a sensor, a bypass valve in the upstream dialysate line is closed or de-energized so that normal flow to the dialyzer is stopped and so that an ultrafiltrate flowmeter is turned off. The isolate valve located downstream of the dialyzer is also closed, so that the dialyzer is isolated between the bypass and isolate valves. Transmembrane pressure ("TMP") alarm limits, operable during normal therapy, are disabled while the dialyzer is isolated. A purge valve located upstream from the bypass valve is opened, allowing post dialyzer fluid sent previously to drain to be drawn through the purge valve to match the flow of fluid to the patient that flows through the balancing chambers or flow equalizer. The volume of fluid flowing to the patient flows through at least one filter, out of a substitution port, is pumped via the substitution pump to the venous drip chamber and through the venous access line to the patient. After the bolus amount is delivered, the purge valve is closed and the patient's blood pressure is allowed to stabilize. Next, the isolate valve is opened, the TMP limits are reset and normal therapy is resumed.

The above apparatus is also suitable to perform a substitution fluid rinseback at the end of therapy to rinse blood remaining in the extracorporeal circuit back to the patient. Here, the operator begins the procedure by pressing a "Rinseback" button and perhaps a "Verify" confirmation input. The rinseback feature, like the bolus volume, can be initiated automatically. An amount of rinseback solution can be preset or set at the time of the procedure. The valve configuration and operation described above is repeated using the bypass valve, isolate valve, TMP alarm limits and purge valve. The substitution pump delivers the programmed rinseback amount to the patient. Again, previously discarded solution is pulled back through the system to balance the fluid flowing to the patient through the match flow equalizer. Here, instead of delivering the amount to the venous dialyzer, as with the bolus solution, the amount is delivered to the arterial access line prior to the arterial drip chamber, so that as much of the extracorporeal circuit as possible is rinsed.

To communicate the substitution pump with the arterial access line, the operator can connect the access line to the second leg of the "Y" connector described above. Or, if the system is used in combination with the pinch clamps described above, the post-dilution clamp is closed and the predilution clamp is opened, allowing for automatic operation.

The machine is set to alert the operator when the rinseback is complete. After the fluid pressures have stabilized, the purge valve is closed, the isolate valve and bypass valve are opened, the TMP limits are activated and treatment is ended per the normal procedure.

In a further aspect of the present invention, the machine uses a ceramic piston rotating reciprocating pump for ultrafiltration ("UF") instead of a more complicated, more accident prone and more expensive diaphragm pump type UF flowmeter assembly. The location of the ceramic pump is predialyzer, immediately downstream of the purge valves. The rotating, reciprocating piston pump is capable of running at a suitable high rate of speed, such as four to eight liters per hour, for rinse and disinfect modes. During therapy, the pump runs at a flowrate equivalent to the desired patient UF rate.

The substitution fluid flow and a volumetric equivalent to the patient's UF is taken from the flow path pre-dialyzer, that is, fresh solution is removed from the system. In one embodiment, the ceramic pump operates with balancing chambers that add and remove an equal volume of fluid to and from the system. Any fluid taken from the system by the ceramic piston pump and any substitution fluid given to the patient as an HDF or an HF infusion is automatically removed from the patient by the post-flow balancing chamber. The fresh solution is removed from the dialysate flow path, therefore, downstream from the balancing chambers so as not upset the balance of same.

There are many advantages to using the ceramic pump and associated flow configuration. The rotating reciprocating ceramic piston pump does not allow flow directly from the input to the output, in contrast to the balancing chamber type UF flowmeter. If the balancing chamber type of UF device fails, there is an uncontrolled flow during half of the cycle, resulting possibly in an overfiltration of the patient. The piston pump of the present invention, on the other hand, is not subject to that type of failure, because its input port does not communicate fluidly with the pump's outlet port. If the pump fails, it fails closed, stopping fluid flow. The piston also prevents purge valve errors from causing a UF error.

The rotations of the pump are monitored using a Reed Switch, optical sensor, flowmeter, tachometer or other type of feedback device, so the pump rotations and the corresponding ultrafiltration volume removed can be checked by an independent mechanism. The pump is placed before the dialyzer, preventing the pump from becoming clogged with organic substances removed from the dialyzer. The pump is, however, placed downstream from at least one membrane filter used to help purify the fresh dialysate. That arrangement provides a continual rinse along the surface of the membranes of the filters. The rinse removes at least a portion of the build-up of bacteria and endotoxin along the membrane surfaces. As a further advantage, the arrangement also removes air from the membrane filters during treatment. The removal of the balancing chamber type UF meter and addition of the rotating, reciprocating pump makes the flow path of the dialysis system simpler, while improving the safety and performance of the equipment. The ceramic piston pump in one embodiment is used to perform the rinseback and bolus infusion features that have been described previously. The pump in those applications operates in the opposite direction so that flow travels to the patient.

In a further aspect, an improved filter configuration and filtration method are provided. The configuration includes at least two filters placed in series between pumps or other hydraulically complicated flow mechanisms. The filter portion of the dialysate flow path is simplified to reduce the accumulation of bacteria and endotoxin. Also, a pump located upstream of the filters is operated to create a higher flowrate than a pump located downstream from the filters. The flow differential also helps to strip accumulated bacteria and endotoxins from membrane surfaces located within the filters as well as tubing connecting the filters.

Each of the above aspects can be employed alone or in any combination with one another.

It is therefore an advantage of the present invention to provide a hemofiltration ("HF") or hemodiafiltration ("HDF") system that can perform both pre- and postdilution clearance modes with a single substitution pump.

It is another advantage of the present invention to provide an HF or HDF system that performs certain net positive fluid flow functions, such as a prime, a bolus function and a rinseback function.

It is a further advantage of the present invention to provide an improved ultrafiltrate flow metering system.

It is yet another advantage of the present invention to provide an HF or HDF system with safety improvement features.

Moreover, it is an advantage of the present invention to provide an HF or HDF system with a simplified flow regime.

Still further, it is an advantage of the present invention to provide an HF or HDF system with performance improvement features.

Yet an additional advantage of the present invention is to provide a HF or HDF system with an improved filtration system and method.

Additional features and advantages of the present invention are described in, and will be apparent from, the following Detailed Description of the Invention and the figures.

DETAILED DESCRIPTION OF THE INVENTION

The present invention provides systems and methods for improving medical fluid delivery systems, such as hemodialysis ("HD"), hemofiltration ("HF") and hemodiafiltration ("HDF") systems. In various embodiments, systems and methods for selectively performing pre- and postdilution HF and HDF clearance modes are provided. In other embodiments, systems and methods for providing bolus, prime and rinseback fluid volumes during/after HD, HF and HDF therapies are provided. In further embodiments, improved systems and methods for removing ultrafiltrate from the patient are provided. Still further, the present invention provides an improved filtration configuration and method.

Pre/Postdilution HDF and HF

Figure 1:
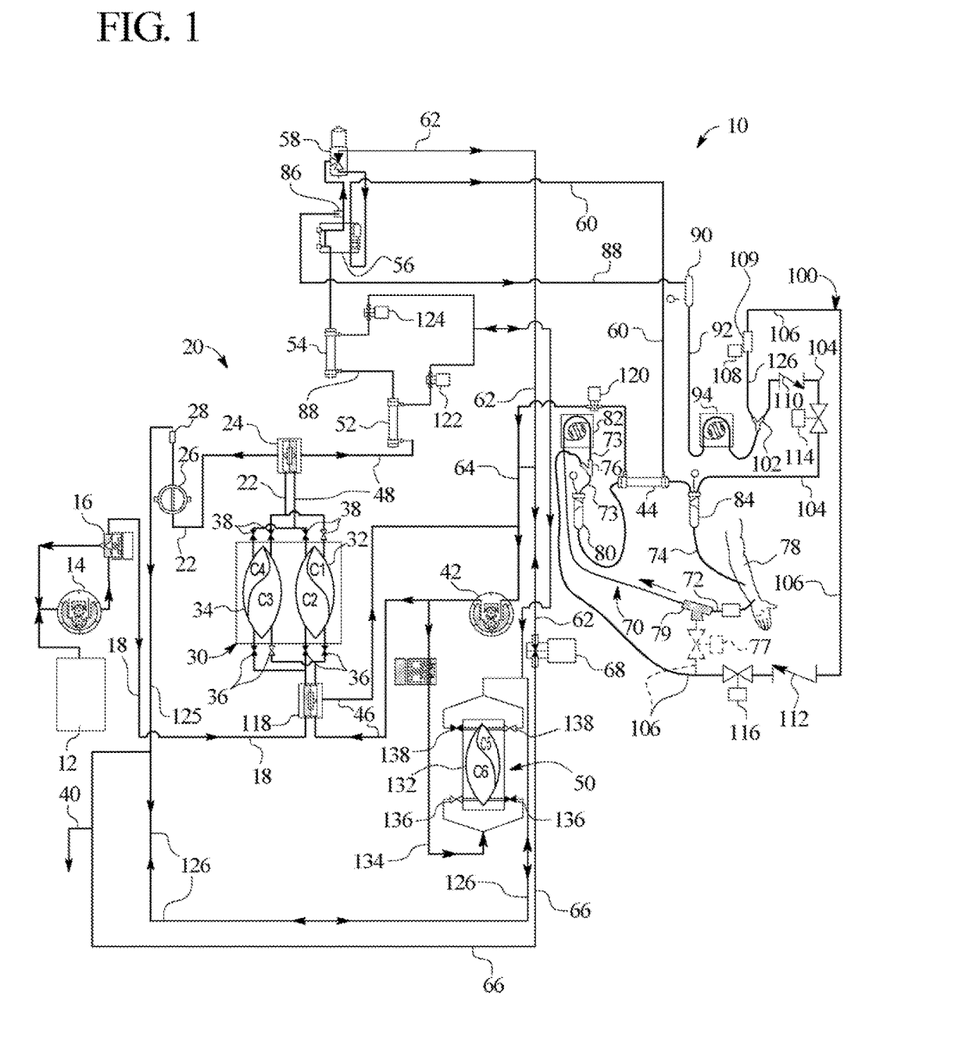
FIG. 1 illustrates systems and methods of the present invention for providing pre- and/or postdilution HF/HDF clearance modes, a bolus volume to the patient, a prime to the patient and/or a blood rinseback volume to the patient.

Referring now to the drawings and in particular to FIG. 1, an HF and/or HDF system 10 is illustrated. System 10 in one embodiment is part of a machine that can perform HD, HF or HDF as selected by a doctor or nurse. The machine is typically used in a treatment center and in one embodiment generates dialysis solution via generation unit 12. One suitable dialysate generation unit 12 for system 10 is described in the maintenance manual for Baxter's System 1000® therapy machine. It should be appreciated from the disclosure herein, however, that the present invention is not limited to dialysate delivery systems or in-center systems but instead applies to any suitable medical fluid therapy treatment.

Whether system 10 operates in an HF or HDF mode, system 10 includes a dialysate flow path 20 and an extracorporeal or blood circuit 70. In dialysate flow path 20, fluid generated via generation unit 12 is pumped via a supply pump 14 through a supply regulator 16, which sets the maximum pressure of the dialysate in the flow path. Dialysate path 20 employs a number of flow control devices that ensure that the desired amount of fluid is delivered to and removed from the patient (described in commonly owned U.S. Pat. No. 5,486,286, the teachings of which are incorporated herein by reference). In particular, dialysate flow path 20 includes a flow equalizer or balancing chamber 30 and an ultrafiltrate flowmeter 50. Flow equalizer 30 includes a pair of fixed volume chambers 32 and 34 that each have a flexible membrane within, creating four variable volume cavities C1, C2, C3 and C4. For fixed chamber 32, the volume in variable cavity C1 is inversely proportional to the volume in variable cavity C2. Likewise, for fixed chamber 34, the volume in variable cavity C3 is inversely proportional to the volume in variable cavity C4.

The two chamber pairs 32 and 34 are provided so that one fixed volume chamber 32 or 34 pumps fluid to the filter/dialyzer, while at the same time, a second fixed volume chamber 32 or 34 pumps an equal amount of fluid from the filter/dialyzer. Match flow equalizer or balancing chamber 30 therefore ensures that any fluid going through equalizer 30 is in turn removed from equalizer 30, resulting in a net fluid gain or loss to the patient of zero. Cavities 32 and 34 also alternate so that in each stroke fluid is pumped to and from the patient, resulting in a steady or non-pulsitile flow profile.

Cavities 32 and 34 operate with inlet valves 36 and outlet valves 38, which are alternated to achieve the above-described flow equalization. In particular, those valves are configured to enable one of the chamber pairs 32 or 34 to receive dialysate flowing through line 18 from regulator 16 to fill one of the cavities C2 or C4. That filling action causes a corresponding one of the cavities C1 or C3 to decrease in volume and thereby push used or spent dialysate that filled cavity C1 or C3 in the previous stroke out line 22, through an output pressure equalizer 24, through a blood leak detector 26 and flow restrictor 28 to drain line 40. While that action is happening, a dialysate pressure pump 42 is pulling spent dialysate from filter/dialyzer 44 and pushing that spent dialysate through a pressure regulating recirculation loop 46 to the other flow chamber pair 32 or 34. Pump 42 pushes fluid into one of the variable spent dialysate cavities C1 or C3.

The increasing volume of spent dialysate in the variable chamber necessarily decreases a like volume of fresh dialysate that filled variable cavity C2 or C4 in the previous stroke, pushing same toward the patient. Fresh dialysate is pushed out line 48, through output pressure equalizer 24, through a first ultrafilter 52, through a portion of filtration line 88, through a second ultrafilter 54 and through a dialysate monitoring manifold 56. Suitable ultrafilter brands are discussed below. From manifold 56, fresh filtered fluid flows either through a three-way bypass valve 58, out bypass valve through line 60 into filter/dialyzer 44 or out through substitution port 86, through the remainder of filtration line 88 and to blood circuit 70.

As illustrated, a second outlet or bypass line 62 extends from bypass valve 58 and extends either into post-dialyzer line 64, leading to pressure regulating recirculation loop 46, or alternatively extends into rinse line 66 and through rinse valve 68 to drain 40. Bypass line 62, rinse line 66 and rinse valve 68 enable various system components to be rinsed or cleaned prior to the beginning of therapy.

Blood circuit 70 includes an arterial access line 72 and a venous access line 74. Arterial access line 72 includes a Y-connection 76 that connects to a dialysate input line described below. Arterial line 72 carries blood from patient 78 to an arterial drip chamber 80. Blood is transferred through extracorporeal circuit 70 via a peristaltic blood pump 82. Pump 82 pumps blood from arterial line 72, through drip chamber 80, to the blood inlet of dialyzer 44. The blood is pumped through the inside of membranes contained within the dialyzer, wherein diffusive transport of toxins and waste products from the blood takes place, and from the output of dialyzer 44 into a venous drip chamber 84, through venous access line 74, and back to patient 78.

Predialyzer dialysate line 60, dialyzer 44, postdialyzer line 64 and the remainder of dialysate flow path 20 are maintained at a pressure lower than that of the blood within circuit 70, resulting in the convective transport of waste out of the membranes within dialyzer 44 and a transport of waste and other undesirable substances from the patient's blood. System 10 is additionally or alternatively capable of performing hemofiltration, in which solution flows along filtration line 88, through substitution port 86, through microfilter/ultrafilter 90, through postfilter line 92, through substitution fluid pump 94 and through a pre/postdilution fluid manifold 100, directly to blood circuit 70.

Figure 2:
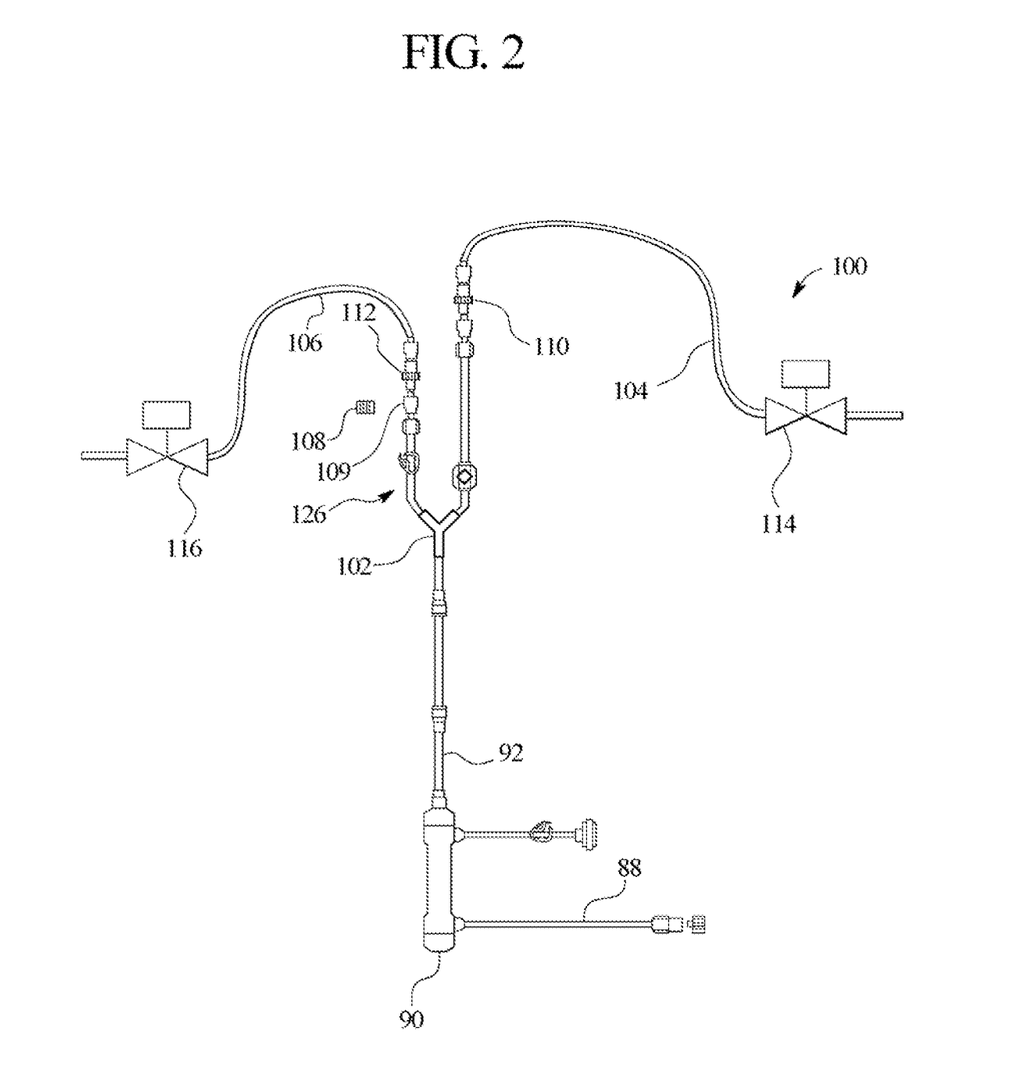
FIG. 2 illustrates one embodiment of a therapy fluid delivery manifold used in the systems and methods shown in FIG. 1.

Referring additionally to FIG. 2 in combination with FIG. 1, pre/postdilution manifold 100 is illustrated in greater detail. Filter 90 in one embodiment is a microfilter. One suitable microfilter is a Pall™ Gelman™ single use 0.22 micron filter. In another embodiment, filter 90 is an ultrafilter. One suitable reusable ultrafilter is a Medica™ Diapure™ 28 filter. One suitable single use ultrafilter is a Medica™ 150u filter. In general, microfilters differ from ultrafilters in the capability of the different filters in removing small particles. In general, ultrafilters can remove smaller particles than can microfilters. For purposes of the present invention, the term "microfilter" includes filters having a membrane pore or membrane opening size of about 1000 to about 105 Angstroms ("Å"), which effectively filters particles, such as red blood cells, yeast, fungi, bacteria and some proteins. The term "ultrafilter" as used herein includes filters having a membrane pore or membrane opening diameter or length of about 10 to about 1000 Å, which effectively filters particles such as endotoxins (pyrogen), viruses and proteins. In one preferred embodiment, the ultrafilters used in the present invention have a range of pore sizes of about 10 to about 40 Å.

Filter 90 operates with ultrafilters 52 and 54 to ensure that a sterile or injectable quality fluid is pumped via substitution pump 94 into the substitution fluid manifold 100. Fluid is pumped via pump 94, through Y-connection 102 into either postdilution line 104 or predilution line 106. A cap 108 is shown removed from a union 109 located at the end of pigtail 126 in line 106. Manifold 100 in an alternative embodiment provides only postdilution line 104 and pigtail 126, wherein remainder of line 106 is removed and the corresponding output from Y-connector 102 is capped off via cap 108. The remainder of line 106 can then be selectively added to pigtail 126 by removing cap 108. When predilution line 106 is fully connected, system 10 can perform either pre- and/or postdilution HF and HDF as desired.

As seen in FIG. 1, postdilution line 104 extends to the venous drip chamber 84. Predilution line 106 extends in one embodiment to a Y-connector or T-connector 76 positioned in a line 73, which is located between pump 82 and drip chamber 80. In an alternative embodiment, line 106 (shown in phantom) extends via a solenoid valve 77 (in phantom) to a second Y-connector or T-connector 79 located in arterial access line 72, which feeds into post-pump line 73. The alternative embodiment is used with a rinseback feature described below. As described in more detail below, it is advantageous to connect predilution line 106 to arterial access line 72 via connector 79 when system 10 is combined with the bolus, prime and rinseback features described below. It should be appreciated however that the predilution therapy operates equally as well with line 106 connected to arterial access line 72 via connector 79 or to line 73 via connector 76.

A check valve 110 is placed in postdilution line 104, which allows fluid to flow only in the direction from pump 94 to blood circuit 70, preventing blood from backing up through lines 92 and 88 into filters 52 and 54 or other parts of dialysate flow path 20. Likewise, a check valve 112 is placed in predilution line 106 to prevent blood from backing into dialysate flow path 20 from predilution line 106.

Postdilution line 104 includes a pinch clamp 114. Predilution line 106 likewise includes a pinch clamp 116. Suitable pinch clamps for system 10 are provided for example by Medica™, Model M03122. Clamps 114 and 116 are electrically operated, pneumatically operated or are otherwise controlled via a microprocessor of system 10 to be opened and closed selectively as specified by the therapy. Manifold 100 of system 10 enables HF or HDF therapy to occur: (i) via postdilution clearance only by opening valve 114 and closing valve 116 throughout therapy; (ii) via predilution clearance only by opening valve 116 and closing valve 114 throughout therapy; (iii) via pre- and postdilution clearance modes by sequentially opening valve 114, while valve 116 is closed and then reversing that state and opening valve 116, while valve 114 is closed; or (iv) via pre- and postdilution clearance modes simultaneously by opening valves 114 and 116 simultaneously.

Although not illustrated, when pre- and postdilution therapy is performed simultaneously, a variable flow restrictor can be placed in either one or both pre- and/or postdilution lines 106 and 104, respectively, to partition the percentage flow of dialysate through lines 104 and 106 as desired (e.g., 80% of flow flows through postdilution line 104, while the remaining 20% flows through predilution line 106). To that end, valves 114 and 116 could instead be needling-type valves that selectively allow a desired percentage flow to pass through lines 104 and 106. Or, such needling valves can be placed in combination with on/off valves 114 and 116, so that there are valved flow restriction settings and on/off control for both pre- and/or postdilution clearance modes.

In one embodiment, the operator sets the overall target substitution volume into the machine employing system 10. The operator then enters a percentage rate or percentage volume of pre- versus postdilution fluid flow. The single substitution pump 94 runs continuously. The clamps 114 and 116 alternate to achieve the desired pre- and postdilution clearance rates. In one example, if the desired percentage breakdown is two-thirds postdilution and one-third predilution and the total flowrate is 150 ml/min, the postdilution clamp could be closed for five seconds, while the predilution clamp 116 is open. Afterward, that state is reversed so that the predilution clamp 116 is closed, while the postdilution clamp 114 is open for the next ten seconds. That sequence is repeated throughout therapy, or at least the portion of therapy that includes convective clearance. Alternatively, flow restrictions are placed in lines 104 and 106 and set to produce the desired two-thirds postdilution of one-third predilution profile, while valves 114 and 116 are opened throughout the convective clearance portion of the therapy.

The goal of diverting some of the convective flow from postdilution to predilution is to prevent hemoconcentration while providing a predominantly postdilution treatment. To that end, it is desirable not to cycle the valves over too long a period so that such a condition could occur. On the other hand, it is also desirable not to cycle the valves too frequently for wear and maintenance purposes. The desired cycle time for the valves is therefore chosen to accommodate both of those factors.

Bolus and Rinseback Functions

Referring still to FIG. 1, a second primary embodiment of the present invention involves the ability of system 10 to perform not only a priming sequence, but to also provide a bolus of fluid to the patient as needed and to perform blood rinseback at the end of therapy. The bolus feature and blood rinseback feature are described hereafter in turn.

Bolus Infusion

To provide a bolus or volume of fluid to the patient, for example, when the patient has lost too much liquid from the patient's vascular system, the bypass valve 58 is set so that dialysate flow no longer flows through predialyzer line 60 but instead bypasses the filter/dialyzer 44 and line 60 and flows alternatively through bypass line 62. Rinse valve 68 is closed so that dialysate flowing through line 62 tees into dialysate return line 64, which shunts the fluid through match flow equalizer 30 to drain 40. The bypass valve 58 configuration has the effect of modifying the dialysate flow path 20 so that dialysate flow bypasses filter/dialyzer 44. As described above, dialysate returning through line 64 is cycled through pressure regulating recirculation loop 46 via dialysate pump 42. Recirculation loop 46 helps to control pressure at the inlet of the flow equalizer 30. In particular, recirculation loop 46 operates with input pressure equalizer 118 and supply regulator 16. Supply pump 14 sets a pressure along line 18. That pressure in line 18 moves a diaphragm within input pressure equalizer 118 back and forth, which either restricts an orifice that builds pressure in loop 46 or opens the orifice lowering the pressure in the loop, which in turn allows more or less fluid to circulate within loop 46.

Besides de-energizing bypass valve 58 so that dialysate flows through bypass line 62, shutting off flowmeter 50, an isolate valve 120 placed in postdialyzer line 64 is closed. Valves 58 and 120 completely isolate filter/dialyzer 44 from the remainder of dialysate flow path 20. To create the bolus volume, with filter/dialyzer 44 isolated, purge valve 122 is opened to drain. At the same time, a portion of the fluid flowing from flow equalizer 30 to bypass valve 58 flows through filtration line 88, out of substitution port 86, through filter 90, through postfilter line 92 and is pumped via substitution pump 94 and postdilution line 104 (or predilution line 106) through venous drip chamber 84, which purges any air from the solution, allowing an injectable quality bolus or volume of fluid to flow into patient 78 via venous access line 74. Since valve 122 is connected to an open source of fluid, namely, from fluid pumped via flow equalizer cavities C1 and C3, through blood leak detector 26, through flow restrictor 28, through line 125 and though line 126 (shown with dual directionally pointed arrows), a volumetric equivalent to the fluid pumped to the extracorporeal circuit 70 via pump 94 can be infused into the system between the pre and post flow equalizers of equalizer 30. After the fluid flows goes through valve 122, the fluid flows through filters 52, 54 and 90 and is monitored for proper conductivity and temperature. Pump 94 will shut down if any of those measurements is outside of a correct range.

The control scheme of system 10 is operable to manually or automatically initiate the bolus volume. In one embodiment, the control scheme automatically commences the bolus feature upon receiving an appropriate signal from a biosensor, such as a hemoconcentration sensor, a blood volume sensor, an electrolyte sensor, an oxygen sensor and any combination thereof.

It is important to note that the transmembrane pressure ("TMP") alarm limits should be disabled or opened during the time that the isolate valve is closed. The TMP alarms in normal operation ensure that there is a positive pressure differential from the blood circuit 70 to the dialysate flow path 20 through dialyzer 44, so that the net flow of liquid is from the blood stream to the dialysate flow path 20. In addition, the TMP is monitored to detect pressure changes that may indicate a problem. When isolate valve 120 is closed, the TMP in dialyzer 44 isolated between valve 120 and bypass valve 58 may tend to equalize. However, because dialysis is not being performed at this moment, such equalization is not a concern and thus the alarms are not necessary.

Flow equalizer 30 requires an equal volume of fluid to flow from line 18 to the equalizer as the volume flowing to equalizer 30 from recirculation loop 46. It should be appreciated that because there is a volume of fluid being delivered to the patient and no fluid can be pulled from the patient with dialyzer 44 isolated, less fluid would return to flow equalizer 30 through line 62, compared to the amount of fresh fluid delivered to flow equalizer 30 from source 12. Accordingly, a makeup source of fluid is needed. For example, if supply pump 14 delivers 300 ml/min to flow equalizer 30 and 100 ml/min is pulled through substitution port 86 to the patient, only 200 ml/min will return through bypass line 62, postdialyzer line 64, recirculation loop 46 to flow equalizer 30. The fluid return is deficient by 100 ml/min with respect to the 300 ml/min global supplied via source 12, and such deficiency will cause flow equalizer 30 to operate improperly.

To provide the additional fluid, purge valve 122, which operates with ultrafilter 52, is opened during the bolus infusion as discussed above. Purge valves 122 and 124 operate normally with ultrafilters 52 and 54, respectively, to enable the filters to be rinsed prior to therapy. Opening purge valve 122 enables the additional needed fluid, e.g., the additional 100 ml/min, to be pulled through lines 125 and 126 and into the dialysate flow path 20. Liquid pulled through drain line 126 has previously flowed through dialyzer 44 and been pumped to drain 40 after passing through flow equalizer 30. Accordingly, the additional fluid pulled through line 126 needs to be sterilized to be of an injectable quality. The filters 52 and 54 and additional disposable filter 90 in filtration line 88 achieve that requirement. That is, fluid entering system 20 through purge valve 122 flows through ultrafilters 52 and 54, out substitution port 86, through a third ultrafilter or microfilter 90 and ultimately to patient 78. Filters 52 and 54 in one embodiment are large surface area, reusable filters. Disposable filter 90 can be an ultrafilter or a microfilter. Placing three filters in series enables system 10 to have triple redundancy during normal operation and for the bolus infusion.

As an extra safety measure, if for some reason the makeup fluid pulled from drain line 126 and passing through both filters 52 and 54 does not produce an injectable quality solution, dialysate monitoring manifold 56, which includes a dialysate conductivity probe, temperature sensor, a flow sensor and a dialysate pressure transducer will trip an alarm upon which substitution pump 94 is shut down. In the event that an alarm is tripped and substitution pump 94 is shut down, the configuration of the peristaltic pump 94 is such that the rotating head clamps the tubing off at a point along the tubing wrapped around the pump head, effectively stopping flow of fluid at that point.

To deliver the bolus volume, the substitution pump 94 pumps the volume through a check valve, such as check valve 110 of post dilution line 104, into venous drip chamber 84. It should be appreciated that pre- and postdilution manifold 100 is not necessary to practice the bolus solution feature of the present invention. However, the bolus solution volume can be implemented via pre- and postdilution manifold 100 discussed above. To do so, pinch clamp 114 is opened to allow the bolus volume to pass through check valve 110, pass by clamp 114 and travel via line 104 to drip chamber 84 or, pinch clamp 116 is opened to allow the bolus volume to pass through check valve 112, pass by clamp 116 via line 106 and travel to drip chamber 80. From drip chamber 80 or 84 the bolus volume travels via venous access line 74 to patient 78.

The amount of the bolus volume is either predetermined or set by the operator upon initiating the bolus function, for example, via a touch screen controller. In one embodiment, the bolus amount is set into the machine employing system 10 via a keypad on the touch screen. The amount of bolus can be controlled, for example, by monitoring the number of rotations of substitution pump 94 or by pumping until a desired setting is achieved on one of the biosensors described above. After the bolus volume is delivered to the patient, isolate valve 120 is opened, purge valve 122 is closed, and bypass valve 58 is energized to allow dialysate to flow through predialyzer line 60, and not to line 62. Opening valves 120 and 58 re-establishes fluid communication with dialyzer 44. The TMP limits are accordingly reset or reopened. Prior to opening isolate valve 120, one stroke can be taken of the UF flowmeter 50 to help create a positive transmembrane pressure when isolate valve 120 is opened. That procedure may be helpful in achieving a set UF target for the patient.

Blood Rinseback

The blood rinseback feature of the present invention operates in a similar manner to the bolus infusion feature described above. The blood rinseback amount can be set at the time the procedure is started or preset according to a prescription or therapy protocol. Again, a touch screen having a keypad can be used to set the rinseback amount. While the rinseback function can be initiated manually in one embodiment, the present invention also contemplates automatically starting the rinseback function at the end of treatment. Further, while the blood rinseback procedure can be controlled by inputting a set amount of fluid, it is also possible to control the feature via a blood detector placed near the patient end of venous access line 74, which detects when no more blood is present in blood circuit 70 and stops substitution pump 94 accordingly and automatically.

Each of the major steps described above for performing the bolus infusion procedure is also performed for the blood rinseback procedure. Obviously, the procedures are performed at different times during therapy because the different procedures are for different purposes. The bolus function as described above is initiated manually or automatically when the patient appears to have become or is becoming hypotensive. Blood rinseback is performed at the end of treatment to push any blood remaining in the system back to patient 78. Nevertheless, both procedures involve the use of isolate valve 120 and bypass valve 58 to isolate dialyzer 44 from the remainder of dialysate flow path 20. Also, purge valve 122 is opened to enable an equal amount of fluid delivered to patient 78 to be drawn via drain line 126, through filters 52, 54 and 90 into dialysate flow path 20, so that flow equalizer 30 operates properly.

One difference between the bolus function and the blood rinseback procedure is the location at which the blood rinseback volume is delivered to extracorporeal circuit 70. As discussed above, the bolus volume can be delivered to venous drip chamber 84. The rinseback amount is delivered on the other hand to the end of or to a point of arterial access line 72 marked by Y-connector or T-connector 79, which is appropriate to clean blood in arterial line 72 through pump 82, through arterial drip chamber 80, through dialyzer 44, through venous drip chamber 84 and finally through venous access line 74 to patient 78. Connector 79 is connected to predilution line 106 via solenoid valve 77 to enable automatic control of the rinseback feature. It is contemplated therefore to use the pre- and postdilution manifold 100 in combination with the rinseback feature of system 10 and to deliver the rinseback volume from substitution pump 94, through Y-connector 102, through predilution line 106, including check valve 112 and pinch valve 116, through line 106 and solenoid 77, to the arterial access line 72 at connector 79.

It should be appreciated, however, that manifold 100 is not necessary to deliver the rinseback volume of the present invention. For instance, the fluid connection can be made manually by the operator or nurse. FIGS. 1 and 2 show a cap 108 that connects to a union 109 located at the end of pigtail 126. It is possible that instead of using the already existing predilution line 106 when the rinseback volume is needed, cap 108 is removed from the union 109 of pigtail 126 and a substitution line (not illustrated) is manually coupled to the end of pigtail 126 and to either connector 79 of line 72 after being uncoupled from the patient or to connector 76 located in line 73, for example, by removing a cap from connection 76. In a preferred embodiment, that substitution line would include at its end a one-way valve or check valve, such as check valve 112.

To couple the substitution line manually to connectors 76 or 79, blood pump 82 is shut down and either a cap is removed from connector 79 or the arterial access line 72 is disconnected from an arterial needle of the catheter that is inserted into patient 78. A clamp is closed at the end of the arterial needle so that no blood is lost from the patient. Connector 76 or 79 is then connected to the substitution line, which is also connected to the end of pigtail 126. In a further alternative embodiment, a luer connector with a rotating hub is provided in one embodiment at the end of arterial access line 72 to couple the line directly to the substitution line extending from pigtail 126. After that connection is made, the rinseback volume is delivered as described above.

The known way to provide a rinseback is to connect a saline bag to the arterial access line 72 after disconnecting such line from the arterial needle. Thereafter, saline flows from the saline bag through the arterial access line 72 to provide the saline rinseback or flush. Both the manual and automatically operating embodiments described above enable system 10 to eliminate the need for a separate saline or injectable solution supply to provide the blood rinseback.

Prime

The prime feature of the present invention operates using the apparatus described above in connection with FIG. 1 for the bolus and rinseback features to prime the extracorporeal circuit 70 prior to therapy. The prime includes a volume of fluid, such as dialysate, that is delivered at the beginning of the therapy to remove air from the extracorporeal circuit. The prime feature is used within a system or with a controller that is operable to receive an operator input to commence delivery of the prime. Alternatively, the system or controller is operable to commence delivery of the prime automatically at the beginning of therapy. In one embodiment, the amount or volume of the prime is entered by an operator when commencing delivery of the prime. The amount or volume can be predetermined prior to commencement of therapy. Alternatively, the amount or volume is delivered until air is no longer sensed in the extracorporeal circuit.

UF Flowmeter

Figure 3:
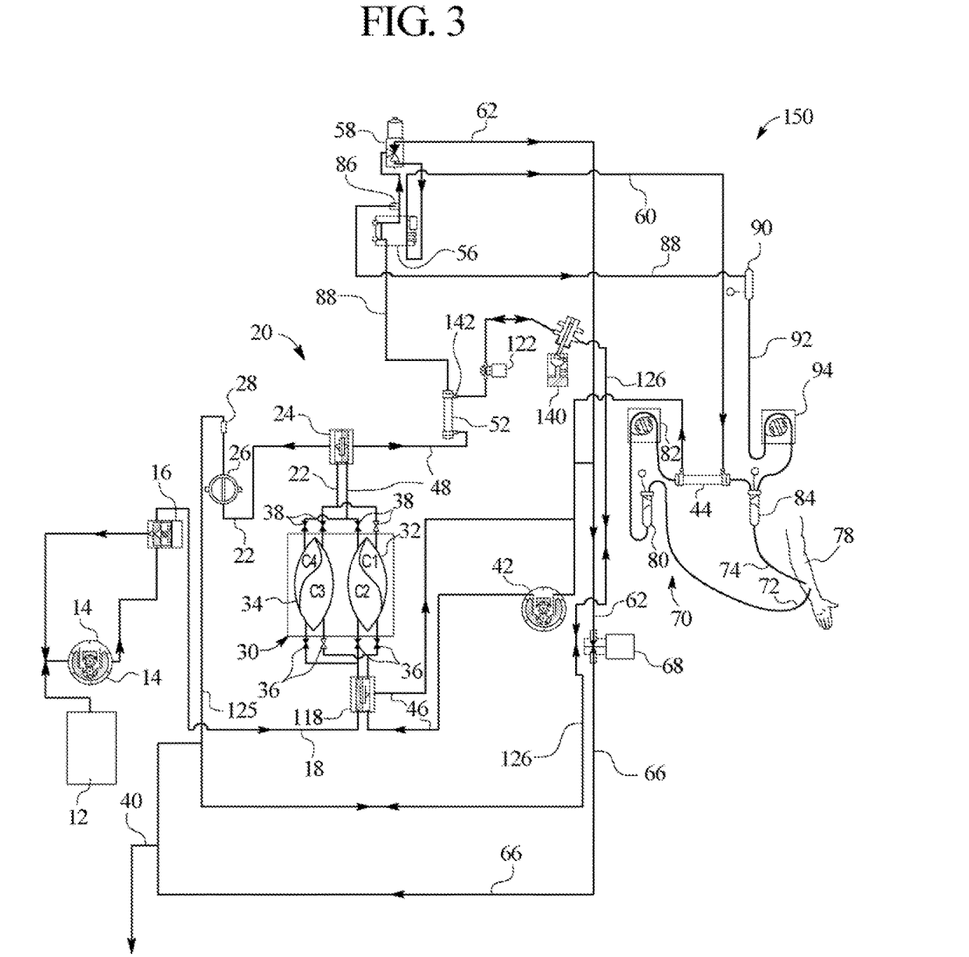
FIGS. 3 and 4 illustrate systems and methods of the present invention for removing ultrafiltrate from the patient and for filtering medical therapy fluid.
Figure 4:
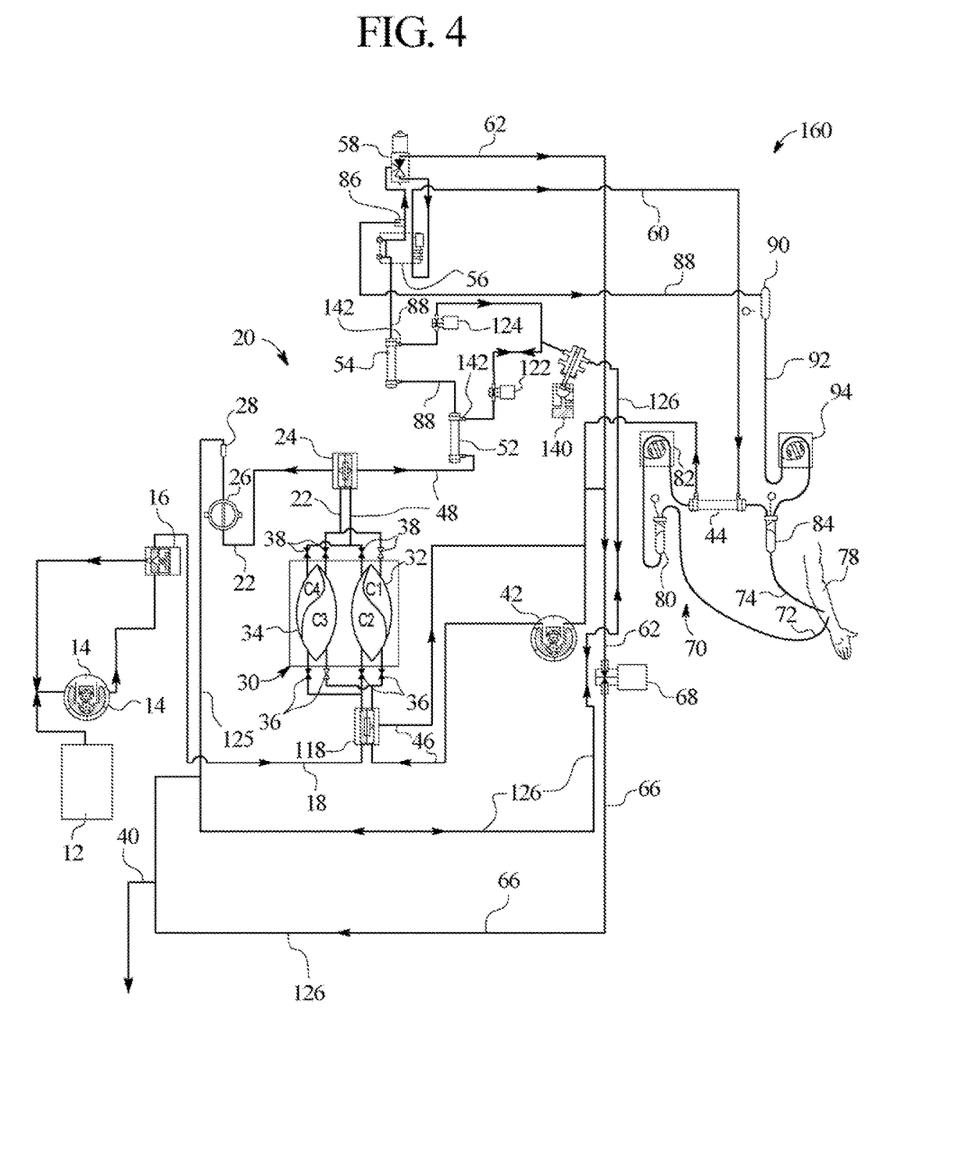

Referring now to FIGS. 3 to 7, another primary embodiment of the present invention is illustrated. FIGS. 3 and 4 illustrate systems 150 and 160, respectively, which include many of the same components described above in connection with FIGS. 1 and 2. Those components are marked with the same element numbers as used in FIGS. 1 and 2. The description of those elements including each of the alternatives discussed above in connection with FIGS. 1 and 2 apply equally to like element numbers in FIGS. 3 and 4.

One primary difference between the embodiments described in FIGS. 1 and 2 compared with the systems 150 and 160 of FIGS. 3 and 4 is that the UF flowmeter 50 is removed in FIGS. 3 and 4. The function of the UF flowmeter so shown in FIGS. 1 and 2 is to remove fluid from the patient 78 that has accumulated in the patient's body over the time between the patient's last therapy and the current therapy. One of the problems that occurs with kidney failure is that the patient in many instances loses some or all of the ability to urinate. The fluid that would otherwise be removed from the patient via urination becomes stored in the patient's blood and surrounding tissues. Thus, while the dialyzer and the infusion of clean solution into patient 78 operate to clear waste products and other undesirable products from patient 78, UF flowmeter 50 operates to remove an additional amount of fluid from the patient, which is equivalent to the amount of fluid gained by the patient between treatments.

UF flowmeter 50 operates in a similar manner to one of the chamber pairs 32 and 34 of flow equalizer 30. UF flowmeter 50 defines a fixed volume chamber 132 that is separated by a diaphragm into two alternating variable volume cavities C5 and C6. Fixed volume chamber 132 is sized in a desired relation to the matched volume chambers 32 and 34. Inlet valves 136 and 138 of UF flowmeter 50 can be cycled with inlet valves 36 and outlet valves 38 of flow equalizer 30. In that manner, a known volume of fluid is removed with each stroke or valve cycle. The valves 136 and 138 alternate so that cavity C6 fills and pushes fluid previously drawn into cavity C5 through one of the outlet valves 138, whereafter the valves switch so that cavity C5 fills and pushes the previously filled volume in cavity C6 through the other outlet valve 138.

UF flowmeter 50 is an effective but relatively complicated device. Also, the failure of one of the valves 136 or 138 can cause an uncontrolled flow during half of a cycle of the diaphragm, resulting in an overfiltration of the patient.

Another potential problem with system 10 illustrated in FIG. 1 is that air can become trapped in ultrafilters 52 and 54. It is possible for air to also become trapped in disposable filter 90, however, it is more likely that air enters reusable filters 52 and 54. Another possible problem with system 10 is that dialysate pump 42 is placed directly in front of a UF removal line 134, which leads to UF flowmeter 50. That configuration can lead to the clogging of UF meter 50. Also, the purge valves 122 and 124 are closed during normal therapy in system 10, so that there is no flow across the outside the membranes of those filters (operational flow through filters is from the inlet of the filters to outside the membranes inside the ultrafilters, through the walls of the membranes, and through the inside of the membranes out the outlet of the ultrafilters). The material that is filtered in filters 52 and 54 remains inside the filters until a rinse cycle is performed after therapy, when purge valves 122 and 124 are opened. That is, bacteria and endotoxin that are filtered by the membranes inside ultrafilters 52 and 54 remain inside those filters throughout the duration of therapy.

Another potential problem in system 10 of FIG. 1 is that the only way to detect if one of the purge valves 122 and 124 is not functioning properly is to detect an increase or decrease in TMP. A TMP error that is not examined and diagnosed properly by an operator could result in a UF error for the patient.

Referring now to FIGS. 3 and 4, the above-described problems are solved by removing UF flowmeter 50 and replacing same with a ceramic UF pump 140 in dialysate flow path 20. Ultra pure dialysate for online HF and online HDF treatments is enabled by locating ceramic pump 140 downstream from the single purge valve 122 in system 150 of FIG. 3 and downstream of dual purge valves 122 and 124 in system 160 of FIG. 4. In both cases, the purge valves are located downstream from the rinse outlet 142 of one of the ultrafilters 52 or 54. Fluid that reaches pump 140 is therefore fluid that is to be removed along drain line 126. As discussed below, pump 140 is a ceramic rotating, reciprocating piston pump in one embodiment, which is advantageous because it does not establish fluid communication between the inlet and outlet of the pump. That pump configuration enables the pump to fail safe, where uncontrolled fluid flow does not occur.

Locating ceramic pump 140 downstream of purge valves 122 and 124 provides additional advantages. That is, besides isolating the inlet and outlet of the pump and thereby eliminating the potential for UF error due to component failure, locating pump 140 predialyzer reduces the possibility of the UF pump becoming clogged or corrupted with organic substances. That is, UF removed to drain from pump 140 is clean or sterile solution from generation unit 12. The likelihood of a UF occurring error due to endotoxin and bacteria building up in the UF removal device is therefore substantially decreased in systems 150 and 160 of the present invention.

Also, because pump 140 pulls fluid from the rinse outlet 142 of filters 52 and 54, systems 150 and 160 provide a continual rinse along the outside of the membranes within those filters. In system 160 of FIG. 4, the purge valves 122 and 124 are cycled, e.g., at fifty percent for each valve, so that both filters 52 and 54 are rinsed and cleaned as therapy takes place. The rinse along the outer surface of the membranes of filters 52 and 54 also removes air from the filters continuously or semi-continuously during treatment. Even though pump 140 removes fresh dialysate as UF, dialyzer 44 functions as described above to diffuse waste products from the patient's blood. Waste is also removed through convective transport caused by the direct infusion of blood into the extracorporeal circuit 70. That waste is then pumped through balancing chambers 30, via dialysate pump 42, to drain. The UF pumping of fresh dialysate via pump 140 does not alter the effectiveness of the therapies of systems 150 and 160.

Figure 5:
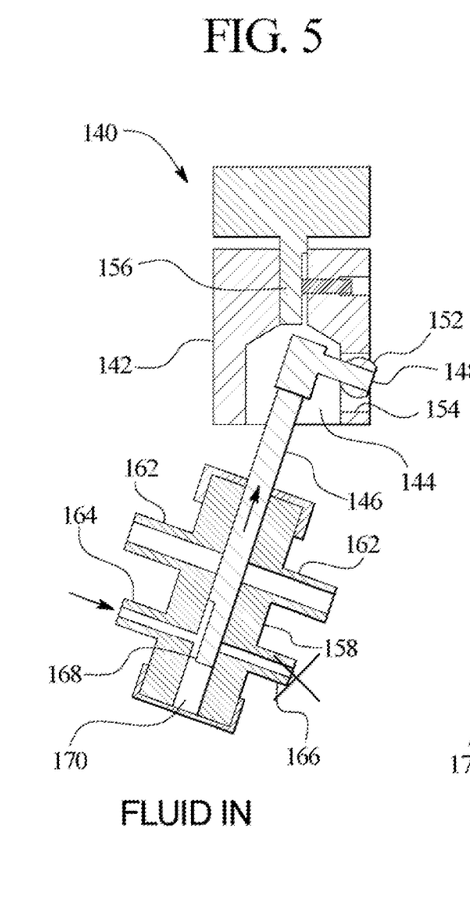
FIGS. 5 to 7 illustrate one embodiment of an ultrafiltrate pump used in the systems and methods shown in FIGS. 3 and 4.
Figure 6:
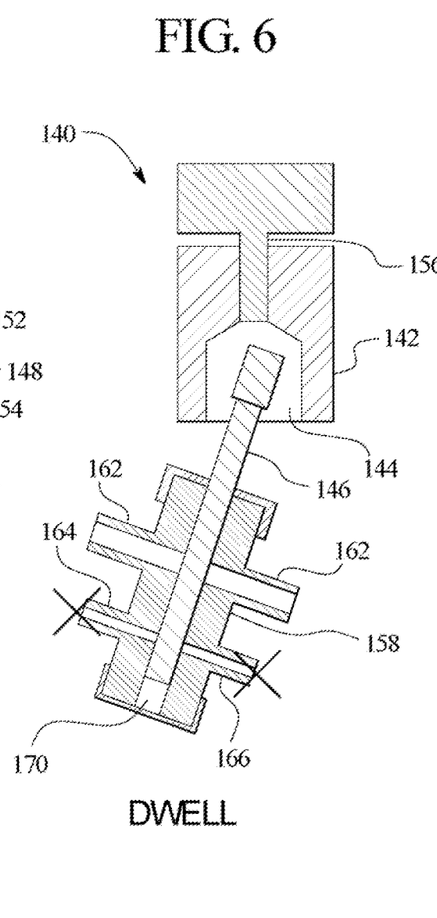
Figure 7:
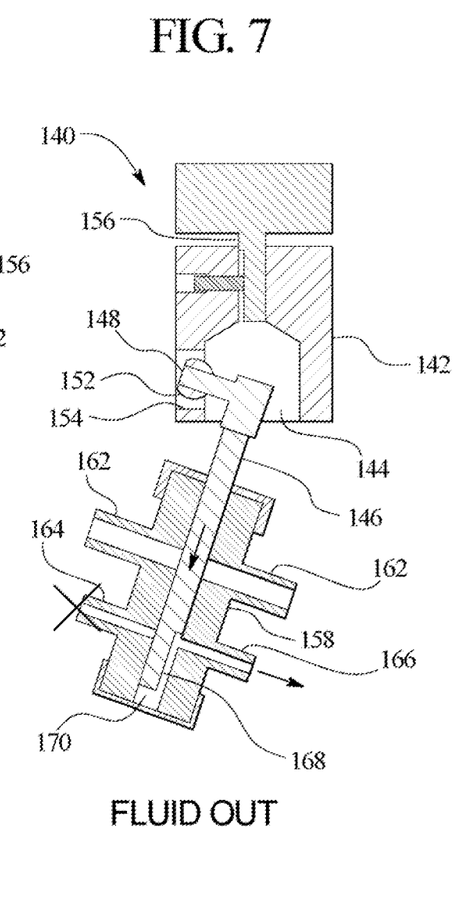

As discussed above, one major advantage with using the ceramic rotating reciprocating piston pump 140 of the present invention is that fluid communication does not exist between the inlet and outlet of UF pump 140. FIGS. 5 to 7 illustrate one embodiment of UF pump 140, which is a rotating and reciprocating piston pump. FIGS. 5 to 7 illustrate the rotating reciprocating piston pump 140 in three states, namely, a fluid-in state in FIG. 5, a dwell state in FIG. 6 and a fluid-out state in FIG. 7. One suitable rotating reciprocating piston pump is supplied by Diener Precision Pumps, Embrach, Switzerland.

In FIGS. 5 to 7, valve 140 includes a rotating chamber 142 defining an opening 144 that receives an end of a rotating and reciprocating piston 146. The end of the piston 146 includes an arm 148 with a ball bearing type head 152 that is received slidingly inside a coupling aperture 154, which is in fluid communication with opening 144. As chamber 142 is rotated via a shaft 156 having a substantially vertical axis, head 152 is carried by the outer wall of coupler opening 154, which in turn rotates arm 148 and shaft 146. Due to the angle of shaft 146 relative to substantially vertical shaft 156, head 152, arm 148 and shaft 146 are also translated in a direction of the angle of shaft 146 back and forth depending on the rotational location of coupler opening 154 during rotation of chamber 142. As illustrated in FIG. 5, during the fluid-in state, piston head 152 is pulled a further distance away from a pump body 158 than the vertical distance between piston head 152 and body 158 in the fluid-out state of pump 140 in FIG. 7. Piston head 152 is accordingly at an intermediate relative distance away from body 158 in the dwell state of pump 140 shown in FIG. 6. It should be appreciated, therefore, that the rotation of drive shaft 156 causes both a rotational motion and translational motion of shaft 146 relative to fixed body 158.

Body 158 defines port openings 162 that enable a lubricant such as water to lubricate the sliding engagement between shaft 146 and the inner bore of body 158. Body 158 also defines inlet and outlet ports 164 and 166, respectively. The lower end of shaft 146 defines a notch 168. Notch 168 in the fluid-in state of pump 140 enables fluid to enter via inlet port 164 into a pump chamber 170. Importantly, in the fluid-in state, no fluid communication exists between pump chamber 170 and outlet port 166. In the dwell state of pump 140 in FIG. 6, shaft 146 has rotated to a position wherein notch 168 does not face or communicate with either port 164 or 166, so that no fluid communication takes place between pump chamber 170 and the openings of ports 164 and 166. In the fluid-out state of pump 140 in FIG. 7, shaft 146 has rotated to a position wherein notch 168 enables fluid communication to exist between pump chamber 170 and outlet port 166. Importantly, in the fluid-out state, no fluid communication exists between pump chamber 170 and inlet port 164.

In operation, as the shaft moves from the fluid-out state (FIG. 7) to the fluid-in state (FIG. 5), the volume in pump chamber 170 increases, creating a vacuum and drawing fluid into chamber 170. In the dwell state (FIG. 6), the volume in pump chamber 170 has decreased from the volume in the fluid-in state (FIG. 5), creating a positive pressure inside chamber 170. As the shaft 146 moves from the dwell state (FIG. 6) to the fluid-out state (FIG. 7), the volume in chamber 170 further decreases and pushes fluid out of outlet port 166.

Because inlet port 164 never communicates fluidly with outlet port 166, pump 140 even upon a failure or loss of power cannot allow an uncontrolled UF flow, decreasing significantly the inherent error potential in comparison to the error inherent in the valves 136 and 138 of prior flowmeter 50 and with the flowmeter 50 itself, as well as potential UF errors that could occur from a failure of one of the purge valves 122 and 124.

As alluded to above, the amount of ultrafiltrate removed from the patient is controlled in one embodiment by monitoring the number of rotations of shaft 146. Rotating, reciprocating piston pump 140 is inherently accurate. If needed, however, a flow measuring device can be placed in drain line 126 to monitor the output of pump 140.

Pump 140 may also be used with each of the embodiments described above in connection with FIGS. 1 and 2, including the pre- and postdilution features, the bolus feature and the rinseback purge. In particular, FIGS. 3 and 4 can employ the manifold 100 discussed above in connection with FIG. 1 however same is not shown for the sake of clarity. To infuse the bolus and rinseback volumes, pump 140 rotates in the opposite direction to pull fluid from line 126 shown with dual directional arrows in FIGS. 3 and 4 in the same manner as discussed above.

Filtration Configuration

The present invention in FIGS. 1 and 4 shows an improved filtration configuration. To produce a suitable replacement fluid for patient 78, an electrolyte solution such as dialysate is filtered by ultrafilters and/or microfilters to achieve an injectable quality output. The present invention employs three filters in series without an intervening pump placed between the filters. The filters each add successive log reduction of bacteria and endotoxin. When a pump is placed between the filters, the pump becomes a place where bacteria and endotoxin accumulate during quiescent times, such as when the system is off. Accordingly, the present invention eliminates the need for placing a pump between the in-series filters. It should be appreciated however that sensors and other flow components besides pumps are contemplated to be placed between the in-series filters.

In an attempt to remove as much bacteria and endotoxin as possible, the present systems shown in FIGS. 1 and 4 uses three filters in series, namely, filters 52, 54 and 90. Those filters help to ensure the quality of the solution by providing successive log reductions of bacteria and endotoxin. Filters 52, 54 and 90 can be any combination of single use or reusable ultrafilters, microfilters or other endotoxin/bacteria reducing devices, such as a clarigen dialguard column. In one embodiment, filters 52 and 54 are reusable and the hydraulics path 88 is constructed without complex hydraulic features, such as a pump, after the first filter in the system, thereby reducing risk of microbial and biofilm growth after the solution is first filtered. In one embodiment, filter 90 is a single use microfilter.

For proper log reduction, it is important to lower the potential for bacteria growth and subsequent endotoxin production. To that end, the filtration configuration of FIGS. 1 and 4 employs no pumps between filters 52, 54 or 90. The flow of medical fluid from filters 52 and 54 passes through sterile tubing (and possibly other flow components) to the inlet of the next filter. Because more complex lumen surfaces of flow components have a greater the chance of forming biofilm, only tubing is provided in one embodiment between filters 52 and 54 and only a single dialysate monitoring manifold 56 is placed between filters 54 and 90. Limiting the components between filters to only simple tubing (and possibly sensor components) helps to prevent the proliferation of bacteria on complex surfaces and to ensure the efficacy of the disinfection.

The purging function during the preparation phase of the medical fluid systems of the present invention also helps to remove bacteria or endotoxin that may have grown since the machine was last used. With the simplified flow path between filters 52, 54 and 90, however, very little growth occurs.

Placing pumps before and after the filters 52, 54 and 90 enables the flowrate of fluid pumped, e.g., via dialysate pump 42, through the filters to be higher than the flowrate pumped, e.g., via infusion pump 94, to the patient 78. The systems of FIGS. 1 and 4 can therefore be set so that that the medical fluid flow to patient 78 is only a portion (albeit a potentially large portion) of the total flow out of the filters, which can be reusable filters. For instance, if the systems are used for hemofiltration and are set to flow 250 ml/min of replacement fluid to patient 78, the flow out of filters 52, 54 and 90 can be 300 ml/min. The purpose for that excess flow is to prevent stagnant areas in the reusable filters at the connections of the filters to filtration line 88, which helps to ensure that during quiescent times bacteria does not proliferate between filters 52 and 54 or after filter 54 in device 56 or filtration line 88.

Due to the use of filters in the above-described manner, the quality of the replacement fluid can be ensured through the combined log reduction of the filters and because the filters to a large extent only have to filter contamination from the incoming medical solution. In addition if one of the filters fails, the resulting log reduction of the remaining filters in most instances is still sufficient to provide a medical grade solution. In addition, the smooth clean surfaces in between the filters are easily and effectively disinfected, preventing growth during quiescent periods. It should be appreciated that while the filtration configuration described herein is particularly well suited for the systems of FIGS. 1 and 4, the configuration is expressly not limited to being used with the other features and inventions described in those figures and indeed is applicable to many different types of injection fluid flow regimes and configurations.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention is claimed as follows:

1. A hemodialysis system configured to return blood to a patient, the hemodialysis system comprising:
a dialyzer;
a dialysis fluid circuit in fluid communication with the dialyzer via dialysis fluid inlet and outlet lines, the dialysis fluid circuit including
a fresh dialysis fluid pump,
a used dialysis fluid pump,
a first balancing unit including (i) a first fresh dialysis fluid chamber operable with the fresh dialysis fluid pump and (ii) a first used dialysis fluid chamber operable with the used dialysis fluid pump, and
a second balancing unit including (i) a second fresh dialysis fluid chamber operable with the fresh dialysis fluid pump and (ii) a second used dialysis fluid chamber operable with the used dialysis fluid pump;
a blood circuit in fluid communication with the dialyzer and including
an arterial line for removing blood from a patient and delivering the blood to the dialyzer,
a venous line for returning blood from the dialyzer to the patient,
a blood pump operable with the arterial line upstream of the dialyzer,
a medical fluid source in fluid communication with the arterial line between a patient end of the arterial line and the blood pump,
a drip chamber located along the venous line;
a blood detector operable with the venous line; and
a blood rinseback scheme wherein, with the dialysis fluid inlet and outlet lines connected to the dialyzer, blood is pushed to the patient via the medical fluid being introduced from its source into the arterial line between the arterial line patient end and the blood pump, and flowed through the dialyzer, through the venous drip chamber and to the blood detector along the venous line, where the medical fluid is sensed by the blood detector to indicate an end of the blood rinseback.

2. The hemodialysis system of claim 1, wherein (i) the first fresh dialysis fluid chamber is located between the fresh dialysis fluid pump and the dialysis fluid inlet line to the dialyzer, (ii) the used dialysis fluid pump is located between the first used dialysis fluid chamber and the dialysis fluid outlet line from the dialyzer, (iii) the second fresh dialysis fluid chamber is located between the fresh dialysis fluid pump and the dialysis fluid inlet line to the dialyzer and (iv) the used dialysis fluid pump is located between the second used dialysis fluid chamber and the dialysis fluid outlet line from the dialyzer.

3. The hemodialysis system of claim 1, wherein the medical fluid source is a substitution fluid source.

4. The hemodialysis system of claim 1, wherein the blood detector is located so as to operate with a patient end of the venous line.

5. The hemodialysis system of claim 1, wherein the medical fluid is introduced from its source into the arterial line via a Y-connector or T-connector located between the arterial line patient end and the blood pump.

6. The hemodialysis system of claim 1, wherein the medical fluid is introduced from its source into the arterial line via a medical fluid line operable with an occluding device, the occluding device opened to enable the medical fluid to be introduced.

7. The hemodialysis system of claim 1, wherein the blood pump is stopped to enable the medical fluid line to be fluidly communicated with the arterial line.

8. A hemodialysis system configured to return blood to a patient, the hemodialysis system comprising:
a dialyzer;

a dialysis fluid circuit in fluid communication with the dialyzer via dialysis fluid inlet and outlet lines, the dialysis fluid circuit including
  a fresh dialysis fluid pump,
  a used dialysis fluid pump,
a blood circuit in fluid communication with the dialyzer and including
  an arterial line for removing blood from a patient and delivering the blood to the dialyzer,
  a venous line for returning blood from the dialyzer to the patient,
  a blood pump operable with the arterial line upstream of the dialyzer,
  a medical fluid source in fluid communication with the arterial line between a patient end of the arterial line and the blood pump,
  a drip chamber located along the venous line;
a blood detector operable with the venous line; and
a blood rinseback scheme wherein, with the dialysis fluid inlet and outlet lines connected to the dialyzer, blood is pushed to the patient via the medical fluid being introduced from its source into the arterial line between the arterial line patient end and the blood pump, and flowed through the dialyzer, through the venous drip chamber and to the blood detector along the venous line, where the medical fluid is sensed by the blood detector to indicate an end of the blood rinseback.

9. The hemodialysis system of claim 8, wherein the dialysis fluid circuit comprises a first balancing unit including (i) a first fresh dialysis fluid chamber operable with the fresh dialysis fluid pump and (ii) a first used dialysis fluid chamber operable with the used dialysis fluid pump, and a second balancing unit including (iii) a second fresh dialysis fluid chamber operable with the fresh dialysis fluid pump and (iv) a second used dialysis fluid chamber operable with the used dialysis fluid pump.

10. The hemodialysis system of claim 8, wherein the medical fluid source is a substitution fluid source.

11. The hemodialysis system of claim 8, wherein the blood detector is located so as to operate with a patient end of the venous line.

12. The hemodialysis system of claim 8, wherein the medical fluid is introduced from its source into the arterial line via a Y-connector or T-connector located between the arterial line patient end and the blood pump.

13. The hemodialysis system of claim 8, wherein the medical fluid is introduced from its source into the arterial line via a medical fluid line operable with an occluding device, the occluding device opened to enable the medical fluid to be introduced.

14. The hemodialysis system of claim 8, wherein the blood pump is stopped to enable the medical fluid line to be fluidly communicated with the arterial line.

15. A hemodialysis system configured to return blood to a patient, the hemodialysis system comprising:
  a dialyzer;
  a dialysis fluid circuit in fluid communication with the dialyzer via dialysis fluid inlet and outlet lines, the dialysis fluid circuit including
    a fresh dialysis fluid pump,
    a used dialysis fluid pump,
  a blood circuit in fluid communication with the dialyzer and including
    an arterial line for removing blood from a patient and delivering the blood to the dialyzer,
    a venous line for returning blood from the dialyzer to the patient,
    a blood pump operable with the arterial line upstream of the dialyzer,
    a medical fluid source in fluid communication with the arterial line between a patient end of the arterial line and the blood pump,
    a drip chamber located along the venous line;
  a blood detector operable with the venous line; and
  a blood rinseback scheme wherein, with the dialysis fluid inlet and outlet lines connected to the dialyzer, blood is transferred to the patient by the medical fluid, wherein the medical fluid is introduced from its source into the arterial line between the arterial line patient end and the blood pump, and flowed through the dialyzer, through the venous drip chamber and to the blood detector along the venous line, where the medical fluid is sensed by the blood detector to indicate an end of the blood rinseback.

16. The hemodialysis system of claim 15, wherein the dialysis fluid circuit comprises a first balancing unit including (i) a first fresh dialysis fluid chamber operable with the fresh dialysis fluid pump and (ii) a first used dialysis fluid chamber operable with the used dialysis fluid pump, and a second balancing unit including (iii) a second fresh dialysis fluid chamber operable with the fresh dialysis fluid pump and (iv) a second used dialysis fluid chamber operable with the used dialysis fluid pump.

17. The hemodialysis system of claim 15, wherein the medical fluid source is a substitution fluid source.

18. The hemodialysis system of claim 15, wherein the blood detector is located so as to operate with a patient end of the venous line.

19. The hemodialysis system of claim 15, wherein the medical fluid is introduced from its source into the arterial line via a Y-connector or T-connector located between the arterial line patient end and the blood pump.

20. The hemodialysis system of claim 15, wherein the medical fluid is introduced from its source into the arterial line via a medical fluid line operable with an occluding device, the occluding device opened to enable the medical fluid to be introduced.

21. The hemodialysis system of claim 15, wherein the blood pump is stopped to enable the medical fluid line to be fluidly communicated with the arterial line.

* * * * *